United States Patent

Mason et al.

[11] Patent Number: 5,863,524
[45] Date of Patent: Jan. 26, 1999

[54] TRANSPARENT BICARBONATE SALT CONTAINING DEODORANT COSMETIC STICK PRODUCT

[75] Inventors: Dawn M. Mason, Hamilton; Melinda G. Cettina, Robbinsville; Wolfgang R. Bergmann, Princeton, all of N.J.

[73] Assignee: Church & Dwight Co., Inc., Princeton, N.J.

[21] Appl. No.: 824,177

[22] Filed: Mar. 26, 1997

[51] Int. Cl.$^6$ ........................................................ A61K 7/32
[52] U.S. Cl. .......................... 424/65; 424/400; 424/401; 424/DIG. 5; 424/78.02; 424/405
[58] Field of Search ........................................ 424/405, 407, 424/65, 78.02, 78.03, 78.05–78.07, 78.18, 78.35, DIG. 5, 400, 401

[56] References Cited

U.S. PATENT DOCUMENTS

| | | |
|---|---|---|
| 4,126,679 | 11/1978 | Davy et al. . |
| 4,382,079 | 5/1983 | Marschner . |
| 4,440,741 | 4/1984 | Marschner . |
| 4,440,742 | 4/1984 | Marschner . |
| 4,534,962 | 8/1985 | Marschner . |
| 4,654,213 | 3/1987 | Ramirez . |
| 4,759,924 | 7/1988 | Luebbe et al. . |
| 4,822,602 | 4/1989 | Sabatelli . |
| 5,114,717 | 5/1992 | Kunitz et al. . |
| 5,128,123 | 7/1992 | Brewster et al. . |
| 5,254,332 | 10/1993 | Grezcyn et al. . |
| 5,302,381 | 4/1994 | Greczyn et al. . |
| 5,354,553 | 10/1994 | Greczyn et al. . |
| 5,376,362 | 12/1994 | Murphy et al. . |
| 5,376,363 | 12/1994 | Benfatto et al. . |
| 5,378,452 | 1/1995 | Greczyn . |
| 5,378,468 | 1/1995 | Suffis et al. . |
| 5,407,668 | 4/1995 | Kellner . |
| 5,424,070 | 6/1995 | Kasat et al. . |
| 5,441,727 | 8/1995 | Chatterjee et al. . |
| 5,443,822 | 8/1995 | Greczyn et al. . |
| 5,486,355 | 1/1996 | Berscheid . |
| 5,508,028 | 4/1996 | Berscheid . |
| 5,567,427 | 10/1996 | Papadakis . |
| 5,597,556 | 1/1997 | Moghe et al. . |
| 5,650,142 | 7/1997 | Bergman ................................ 424/65 |

OTHER PUBLICATIONS

CTFA International Cosmetic Ingredient Dictionary, Fourth Edition, 1991, pp. 50, 288–290, 582, 694, & 978.
LUPASOL™ Product Literature, BASF, Sep. 1997, 1 page.
LUPASOL™ P Product Literature, BASF, Aug. 1987, 1 page.
LUPASOL™ PL Product Literature, BASF, Aug. 1997, 1 page.
LUPASOL™ SC® Product Literature, BASF Sep. 1997, 1 page.
LUPASOL™ SC®–61B Product Literature, BASF Aug. 1997, 1 page.
LUPASOL™ SKA Product Literature, BASF Aug. 1997, 1 page.
Product Literature From Olin Chemicals.

*Primary Examiner*—Neil S. Levy
*Attorney, Agent, or Firm*—Irving Fishman

[57] ABSTRACT

The present invention is a transparent deodorant cosmetic stick product with at least 3.5% by weight of the formulation being an alkali metal bicarbonate. The product contains about 1.25% to about 6.5% of a polyamine as a mandatory clarifying component. Other required components of the formulation are a polyhydric alcohol, a $C_{14-22}$ fatty acid salt, of a clarifier surfactant, and less than about 42% by weight water. Optional ingredients include antibacterial or bacteriostatic agents, a silicone copolyol, zinc pyridinethiol oxide, fragrance and color.

24 Claims, No Drawings

TRANSPARENT BICARBONATE SALT CONTAINING DEODORANT COSMETIC STICK PRODUCT

CROSS REFERENCE TO RELATED APPLICATIONS

The subject matter of the present application relates in part to the subject matter of U.S. Ser. No. 8/503,939, filed Jul. 19, 1995; U.S. Ser. No. 8/526,269, filed Sep. 13, 1995; and U.S. Ser. No. 8/534,819, filed Sep. 27, 1995, all of which are incorporated herein by reference.

BACKGROUND OF THE INVENTION

Numerous solid antiperspirant and/or deodorant compositions are described in the chemical and cosmetic literature. These compositions are generally emulsion sticks or suspensoid sticks. Emulsion sticks contain a solution of the antiperspirant and/or deodorant ingredient incorporated into the stick via an emulsion. Although emulsion sticks are desirable in certain respects, they tend to be unstable, exhibit tackiness, and leave a visible residue on the skin after use. Suspensoid sticks contain the powdered antiperspirant and/or deodorant ingredient suspended in the stick without the use of water or an emulsion. While suspensoid sticks have stability, they tend to leave a white, chalky residue on the skin after application.

With respect to deodorant activity, sodium bicarbonate has long been recognized for its deodorant properties, and has commonly been used as a household deodorant. Plain powdered sodium bicarbonate, or sodium bicarbonate diluted with talc or other filler, has been used as an underarm deodorant as disclosed in U.S. Pat. No. 4,382,079. Other publications which describe cosmetic stick compositions containing a bicarbonate deodorant include U.S. Pat. No. 4,822,602, U.S. Pat. No. 4,832,945, and U.S. Pat. No. 4,440,742, all of which are incorporated herein by reference.

However, the development of a practicable and effective composition in cosmetic stick form which has deodorization capacity, and which is capable of consumer acceptability, presents many factors that are unique. Because sodium and potassium bicarbonate have only limited solubility in water, alcohol, and other solvents, the preparation of a composition suitable for dispensing in cosmetic stick form has involved many processing obstacles. In addition to the problem of limited solubility, sodium bicarbonate often is incompatible with other ingredients of conventional stick compositions. Also, the dimensional stability of the cosmetic stick containing sodium bicarbonate, and the esthetic appearance and the "feel" on the skin, are just a few of the additional difficulties encountered in the preparation of a low-residue, deodorant, cosmetic stick product.

A recent trend is toward the development of cosmetic sticks that have light transmitting properties, i.e., the cosmetic sticks are translucent or transparent in light transmitting properties, and engender a perceived appearance of purity.

Cosmetic sticks which are soap-based and which have a content of sodium bicarbonate as a deodorant ingredient typically are opaque in appearance. U.S. Pat. No. 4,440,742 describes anhydrous and water-based deodorant cosmetic sticks which contain sodium bicarbonate, and which vary from opaque to transparent in appearance as determined by the proportions of sodium bicarbonate and water, in combination with other ingredients.

U.S. Pat. No. 5,424,070 describes a transparent solid stick composition containing ingredients such as propylene glycol, water, sodium stearate and Eumulgin L.

There are difficulties associated with the preparation of water-based cosmetic stick products which contain sodium bicarbonate as a deodorant ingredient. Thus, the transparency properties do not have long-term stability. Acceptable degrees of hardness and smoothness are not readily achieved, and an unpleasant cool-wetness is experienced when the cosmetic stick is applied to the skin surface.

As such, there is a continuing interest in the development of water-based deodorant cosmetic stick products which have a high degree of consumer acceptance.

In pursuing this objective, various clarifying substances have been utilized to render an opaque stick translucent or a translucent stick transparent. Unfortunately, these efforts have not been very successful. As can be seen from most of the patents mentioned above, the standard clarifying surfactants have not been able to reliably render sodium bicarbonate containing deodorant stick products transparent. Therefore, there remains a need for a different type of clarifier ingredient for incorporation into alkali metal bicarbonate containing deodorant stick products.

Complexing agents such as polyfunctional polymeric materials have the ability to solubilize a number of substances. One class of substances that has been used in formulations (other than deodorant sticks) which contain sodium bicarbonate are the polyalkylenimines. These materials have been mentioned in formulations in the dental care area, primarily in dentifrice formulations, as complexing agents for a zinc compound. See for example U.S. Pat. No. 4,022,880; U.S. Pat. No. 4,082,841; U.S. Pat. No. 4,522,806, and U.S. Ser. No. 8/269,155, filed Jun. 30, 1994 (now allowed), all of which are incorporated herein by reference. Of special note is the last mentioned allowed U.S. patent application, as that patent also contains sodium bicarbonate and there is no deleterious effects on the sodium bicarbonate by virtue of incorporating the polyamine. It should be especially noted that the purpose of the polyamine compound in all of the foregoing patents is to solubilize a zinc containing compound. There is no teaching or suggestion in any of these patents that the polyamine would have any effect on the light transmittance properties of an alkali metal bicarbonate formulation which, in the absence of both the zinc compound and the polyamine, would otherwise not be transparent.

OBJECTS OF THE INVENTION

Accordingly, it is an object of the invention to provide cosmetic stick product which is a water-based composition having an effective deodorizing amount of alkali metal bicarbonate salt.

It is another object of the present invention to provide a bicarbonate salt-containing deodorant cosmetic stick product having stable transparency and affording a comfortable dry feel when applied to a skin surface.

It is another object of the invention to provide a high alkali metal bicarbonate content deodorant cosmetic stick product which has suitable processing capabilities.

Other objects and advantages of the present invention will be apparent to those of ordinary skill in the art given the accompanying description and examples.

SUMMARY OF THE INVENTION

These objectives and others are accomplished by a deodorant cosmetic stick product comprising (1) an amount of an alkali metal bicarbonate and/or an alkali metal carbonate so as to satisfy the equation:

7.0<(2(alkali metal bicarbonate wt %)+(alkali metal carbonate wt %))≦11.0;

(2) about 35% to about 55% by weight of a polyhydric alcohol; (3) about 1.25% to about 8.0% by weight of a polyamine clarifier; (4) about 1.25% to about 5% by weight of a $C_{14-22}$ fatty acid salt; and (5) water in an amount less than about 42% by weight; and optionally (6) one or more ingredients selected from the group consisting of an underarm deodorant acceptable antibacterial or bacteriostatic agent, a silicone copolyol; zinc pyridinethiol oxide, fragrance, color, and about 2% to about 10% by weight of a clarifier surfactant.

DETAILED DESCRIPTION OF THE INVENTION

The present invention formulation comprises:

(1) an amount of an alkali metal bicarbonate and/or an alkali metal carbonate or alkali metal salt which is convertible in situ into said alkali metal bicarbonate or carbonate so as to satisfy the equation:

7.0<(2(alkali metal bicarbonate wt %)+(alkali metal carbonate wt %))≦11.0;

(2) about 35% to about 55% by weight of a polyhydric alcohol;

(3) about 1.25% to about 8.0% by weight of a polyamine clarifier;

(4) about 1.25% to about 5% by weight of a $C_{14-22}$ fatty acid salt; and (5) water in an amount less than about 42% by weight; and optionally (6) one or more ingredients selected from the group consisting of an underarm deodorant acceptable antibacterial or bacteriostatic agent, a silicone copolyol; zinc pyridinethiol oxide, fragrance, color and about 2% to about 10% by weight of a clarifier surfactant. All weight percents as used herein are based on the finished stick product weight unless the context requires or the text specifically states otherwise.

The alkali metal bicarbonate ingredient is selected from sodium bicarbonate and potassium bicarbonate and mixture thereof. The alkali metal carbonate ingredient is selected from sodium carbonate and potassium carbonate. It is also intended that the carbonate and bicarbonate species can be formed in-situ, especially from in situ conversion from the other of the corresponding bicarbonate and/or carbonate species.

The bicarbonate-salt functions as a deodorant-active ingredient when a cosmetic stick of the invention is applied to underarm skin. The bicarbonate salt ingredient combats malodors by absorbing the objectionable byproduct resulting from bacterial degradation of perspiration constituents.

The transparency of an invention cosmetic stick product is directly dependent upon the proportions of dissolved and undissolved bicarbonate salt in the cosmetic stick matrix. When a cosmetic stick has a content of about 3% by weight of bicarbonate salt, the cosmetic stick (absent the polyamine ingredient discussed below) is translucent when the water content is between about 20% and about 50% by weight. Depending on the content of other ingredients which can function as clarifying agents to a limited degree, transparency can generally be achieved when the water content is greater then 50% by weight, usually 50%–80% by weight. Unfortunately, such a high water content results in a number of consumer unacceptable properties, especially soft sticks and/or a cool-wet feel on application to the skin.

When the bicarbonate ingredient is present without the carbonate ingredient, the present invention preferably contains at least 3.5% by weight alkali metal bicarbonate, more preferably at least about 4.0% by weight, even more preferably at least 4.25% by weight, still more preferably at least about 4.4% by weight, and most preferably about 4.5% by weight alkali metal bicarbonate. While the upper limit of the alkali metal bicarbonate is limited only by the need to include other components, it is preferably less than about 5.5% by weight, more preferably less than about 5.0% by weight. When the carbonate ingredient is present without the bicarbonate ingredient, it is preferably present in at least 7.0 weight %, more preferably at least 8.0 weight %, still more preferably 9.0 weight %. The upper limit of the carbonate ingredient when the bicarbonate ingredient is absent is about 11.0 weight %, preferably about 10.0 weight %. When used in combination, 2(bicarbonate wt %)+(carbonate weight %) should be at least about 7.0%, preferably at least about 8.0%, more preferably at least about 8.9%, and generally less than about 11.0%, preferably less than about 10.0%, more preferably less than about 9.1%; most preferably 2(bicarbonate wt %)+(carbonate wt %) is about 9.0%.

While any alkali metal bicarbonate or alkali metal carbonate salt is suitable, sodium bicarbonate is preferred. Other (non-alkali metal) carbonates and bicarbonates may be used to generate the alkali metal bicarbonate in situ and still be within the present invention.

As used herein, the term "transparent" refers to a clear body which has the property of transmitting visible light without appreciable scattering, so that an object placed beyond the transparent body is visible and distinguished when looking through the transparent body. The term "translucent" refers to a body which transmits visible light, but has appreciable visible light scattering and/or visible light diffusion so that in attempting to view through the body an object placed beyond the body, the object cannot be clearly distinguished, even with the aid of additional lighting. The term "opaque" refers to a body which does not transmit visible light.

The polyhydric alcohol component is selected from organic compounds which contain about 2 to about 6 carbon atoms and about 2 to about 6 hydroxy groups. Illustrative, but not limiting, of polyhydric alcohols are ethylene glycol, propylene glycol, trimethylene glycol, butylene glycol, diethylene glycol, dipropylene glycol, glycerin, sorbitol, and the like, and mixtures thereof. Preferred polyhydric alcohols are those which are water miscible in all proportions such as ethylene glycol, propylene glycol, diethylene glycol, dipropylene glycol, and glycerin. A highly preferred polyhydric alcohol is propylene glycol. A preferred mixture is predominately propylene glycol with a minor amount of dipropylene glycol.

The polyhydric alcohol is present in an amount of from about 35% to about 55% by weight, preferably from about 35% to about 52.5% by weight, more preferably from about 37% to about 50% by weight, still more preferably from about 38% to about 45% by weight and most preferably from about 38.5% to about 42% by weight.

One of the objects set out above is the provision of a transparent deodorant stick product having an amount of alkali metal bicarbonate and or alkali metal carbonate such that 2(alkali metal bicarbonate wt %)+(alkali metal carbonate wt %)≧about 7.0 while maintaining a limited water content. Surprisingly, the inclusion of the polyamine component allows one to achieve this objective (as well as the other object of the invention).

Polyamines suitable for the polyamine clarifier component include water-soluble chemical structures such as polyalkylenamines (and especially the polyalkylenimines) having a weight average molecular weight between about 800 and about 1,000,000. A preferred group of such compounds corresponds to the structure I:

where R1 is hydrogen or a $C_{1-3}$ alkyl group and n is an integer of from 2 to 6, preferably from 2–4, most preferably 2. The polymer may be a homopolymer or a copolymer of different monomeric units fitting the above description. When the polymer is a copolymer, the differing units may be arranged in random or block copolymer fashion. Other monomeric units which are copolymerizable (but do not correspond to formula I above) may be included, but preferably do not exceed 10% of the monomeric units of the polymer. Preferably, the polyamine is a homopolymer of formula I above, wherein R1 is hydrogen, n is 2. The average number of repeating units of formula I in the polyalkylenimines is from about 750 to about 2250, preferably from about 1000 to about 2000, more preferably from about 12250 to about 1750, still more preferably from about 1450 to about 1550, and most preferably about 1500. Other polyamines which may be suitable for use in the invention have a comparable number of repeating amine containing units and a comparable molecular weight to the polyalkylenimines (of formula I) described above.

The polyamine clarifier component is typically present in an amount of from about 1.25% to about 6.5% by weight, preferably from about 1.9% to about 5.5% by weight, more preferably from about 2.5% to about 4.4% by weight, still more preferably from about 2.5% to about 3.5% by weight, and most preferably about 3% by weight.

The fatty acid salt component is generally a hardener/gelling agent. It is preferably selected from $C_{14-22}$ fatty acid salts. Suitable fatty acid salts include alkali metal, alkaline earth metal, aluminum, and amine salts of fatty acids such as myristic, palmitic, stearic, behenic, oleic, linoleic, linolenic, and the like, and mixtures thereof. Illustrative specific fatty acids include sodium stearate, potassium stearate, aluminum monostearate, sodium oleate, sodium palmitate, sodium behenate, diethylamine stearate, triethylamine stearate, triethylemine oleate, and the like. Especially preferred is sodium stearate. The fatty acid salt component is present in an amount of from about 1.25% to about 5% by weight, preferably from about 2% to about 4% by weight, more preferably about 2.4% to about 3.6% by weight, and most preferably about 2.5% to about 3.5% by weight.

The clarifier-surfactant component is a hydrophilic clarifier surfactant and is selected from pentadoxynol-200 (RTD Chemicals Corp), tetra(hydroxypropyl)diamine (Quadrol, BASF), 2-amino-2-methylpropanol (AMP, Angus Chemical Company), 2-amino-2-hydroxymethyl-1,3-propanediol (Tromethamine, Sigma Chemical Company), and the like, as well as from poly($C_{2-4}$alkylene) glycol ethers of $C_{12-22}$ fatty alcohols, where the oxyalkylene radical imparts hydrophilic properties to the clarifier. The $C_{12-22}$ radical is preferably derived from alcohols which include lauryl alcohol, myristyl alcohol, palm alcohol, stearyl alcohol, and behenyl alcohol.

The alkylene group of the polyalkylene glycol portion is preferably ethylene or propylene, more preferably 1,2-ethylene or 1,2-propylene. The polyalkylene glycol portion may be a homopolymer or a mixed polymer of these alkylene oxide units. When a mixed polymer is desired, it may be a block or random copolymer. Preferably it is an ethylene oxide homopolymer. The number of repeating units in the polyalkylene glycol portion may vary from 10 to about 100, although a wider range of polyalkylene portion repeating unit containing molecules may be suitably used when desired without departing from the spirit of the invention.

The term "hydrophilic" as used with respect to the clarifier-surfactant refers to an HLB of at least 10 or higher. Illustrative of these polyethylene glycol fatty alcohol ethers are the Laureth and Steareth types of polyethylene glycol ethers, which include commercial products such as Dehydol 100 (Henkel), Marlowet LMA 10 (Huls America), Unihydrol 100 (UPI), Emalex 720 (Nihon Emulsion), Procol LA-20 (Protameen), Marlipal 24/300 (Huls America), Procol LA-40 (Protameen), PEG-10 Myristyl Ether, Brij 76 (ICI Americas), Unicol SA-10 (UPI), Lipocfol S-20 (Lipo), Hodag Nonionic S-20 (Hodag), Brox S-30 (Brooks), Unicol SA-40 (UPI), PEG-50 Stearyl Ether, Brij 700 (ICI Americas), Nikkol BB-20 (Nikko), and the like; and similar hydrophilic polyethylene glycol ethers listed in the CFTA International Cosmetic Ingredient Dictionary (Fourth Edition), incorporated herein by reference. Combinations of clarifier surfactants employing some components having an HLB below about 10 are also permissible provided that when taken as a whole, the clarifier-surfactant component has an HLB of about 10 or higher. Preferably, the clarifier component is pentadoxynol 200. This component is present in an amount of from about 2% to about 8% by weight, preferably from about 2.25% to about 5% by weight, more preferably from about 2.4% to about 3% by weight, still more preferably about 2.45% to about 2.6% by weight, most preferably about 2.5% by weight.

A present invention stick product typically has less than about 42% by weight water, although greater amounts (up to about 49.5%) can be present when extremely high amounts of bicarbonate and/or carbonate ingredient are being incorporated. Preferably, the invention stick product has a water content of less than about 41.9% by weight, still more preferably less than about 41.8% by weight. The invention calls for water to be present in an amount of at least 20% by weight, preferably at least 25% by weight, more preferably at least 26% by weight, even more preferably at least about 26.25% by weight. In particularly preferred embodiments, the water content is about 26.25% to about 41.82% by weight.

In addition to the above required components, the present invention sticks can have any of a number of underarm deodorant stick product acceptable additives. These include hydrophilic silicone-copolyol clarifier-surfactant, antibacterial or bacteriostatic agents, fragrance, color, and zinc pyridinethiol oxide, among others.

Illustrative of hydrophilic silicone-copolyol clarifier-surfactant ingredients are dimethicone copolyol type of polymers, which include commercial products such as Dow Corning 193, GE SF-1288, Abil B 8847 (Goldschmidt), Alkasil NE 58-50 (Rhome-Poulenc), Amersil DMC-287 (Americol), KF 353A (Shin Etsu), Masil 1066D (PPG/Mazer), Silicone Copolymer F-754 (Wacker), Sibwet L-7000 (Union Carbide), and the like; and similar hydrophilic silicone polyols as listed in the CTFA International Cosmetic Ingredient Dictionary (Fourth Edition), incorporated herein by reference. Especially preferred is GE SF1288 Silicone (dimethicone copolyol). The hydrophilic silicone copolyol ingredient may be present up to about 6% by weight, preferably up to from about 2% to about 5% by weight, more preferably about 3% to about 4.75% by weight, still more preferably about 4.0% to about 4.65% by weight, and most preferably about 4.5% by weight.

Illustrative of the antibacterial and bacteriostatic agents are Triclosan (Ciba-Geigy), Chloracel (Reheis Chemical Company), zinc phenolsulfonate, dichloro-m-xylenol, sodium N-lauroyl sarcosinate and the like. Triclosan is preferred. These agents may be present up to about 0.5% by weight, preferably from about 0.1% to about 0.4% by weight, more preferably from about 0.25% to about 0.3% by weight, most preferably about 0.28% by weight.

Fragrance may be incorporated in amounts of up to about 3% by weight, typically 0.1% to about 3% by weight, preferably about 0.75% to about 2% by weight, more preferably about 1% to about 1.75% by weight. 1% and 1.5% by weight are particularly preferred. The fragrance can be any fragrance desired so long as it does not adversely affect the clarity of the cosmetic stick product. Specific fragrances are illustrated by linalyl acetate, isopropyl myristate, cedryl acetate, myrcenyl acetate, and other compounds such as those listed in U.S. Pat. No. 5,114,717, incorporated herein by reference, as well as mixtures of any of the foregoing.

Colorants may also be present in amounts up to about 0.5% by weight, preferably about 0.05% to about 0.375% by weight, more preferably about 0.075% to about 0.15% by weight, most preferably about 0.1% by weight. Colorants may be selected from any of the cosmetically approved colorants as may typically be found in the CTFA International Dictionary of Cosmetic Products (Fourth Edition), incorporated herein by reference.

Zinc pyridinethiol oxide (available commercially under the name zinc omadine from Olin), when present replaces an approximately equal weight of propylene glycol in the above invention stick products. When present, zinc omadine is used in amounts of up to about 1.5% by weight, preferably from about 0.1% to about 1% by weight, more preferably about 0.2% by weight.

A present invention deodorant cosmetic stick product can be produced by blending the ingredients in various orders of addition, although the prescribed fashion set forth below is preferred.

In the general preferred method of blending the ingredients, the water (preferably distilled or deionized) is added to a first vessel and heated to about 60° C. The polyalkyleneamine component is then added to this vessel and mixed well. While maintaining the vessel contents at 60° C., the zinc compound (if present) is added to the polyalkylenamine solution. Alternatively, the zinc compound and the polyalkylenamine order of addition can be reversed.

In a second vessel, the propylene glycol is heated to about 80° C. Then, triclosan (if present) is added to the second vessel while the vessel contents are maintained at about 75°–80° C. Next, the pentadoxynol-200 (if present) is added to the second vessel and allowed to completely dissolve while the vessel contents are maintained at about 80° C. Next, the dimethicone copolyol component is added to the second vessel.

The bicarbonate and/or carbonate component is then added to vessel 1 while the sodium stearate is added slowly, using a spatula, to vessel 2. At this point, the contents of vessel 1 is slowly added to vessel 2. The resulting mixture is allowed to cool to 65° C. to 70° C., whereupon the color and fragrance are added. The resulting mixture is poured into canisters and bubbles are removed using a heat gun.

The following examples illustrate, but do not limit, the invention. The components and specific ingredients are presented as being typical, and various modifications within the scope of the invention can be derived by those of ordinary skill in view of the present disclosure.

EXAMPLE I

This Example illustrates a plain vanilla stick product within the present invention.

| INGREDIENTS | PARTS BY WEIGHT |
|---|---|
| D.I. water | 40.789 |
| Sodium Bicarbonate Grade 3 (Church & Dwight) | 4.961 |
| Polymin-P (polyethylenimine by BASF) 50% active solids | 6.614 |
| Propylene Glycol | 44.703 |
| OP-100V (sodium stearate by RTD Chemicals Corp) | 2.932 |

The ingredients are blended in the manner set forth above to yield a clear, transparent cosmetic deodorant stick product of the invention.

EXAMPLE II

This Example illustrates a cosmetic stick product within the present invention, with an antibacterial and optional silicone polyol components present.

| INGREDIENTS | PARTS BY WEIGHT |
|---|---|
| D.I. water | 38.813 |
| Sodium Bicarbonate Grade 3 (Church & Dwight) | 4.720 |
| Polymin-P (polyethylenimine by BASF) 50% active solids | 6.294 |
| Irgasan DP200 (triclosan by Ciba-Geigy) | 0.294 |
| Propylene Glycol | 42.536 |
| OP-100V (sodium stearate by RTD Chemicals Corp) | 2.622 |
| GE 1288 (dimethicone copolyol) | 4.720 |

The ingredients are blended in the manner set forth above to yield a clear, transparent cosmetic deodorant stick product of the invention.

EXAMPLE III

This Example illustrates a cosmetic stick product within the present invention, with an antibacterial, optional silicone polyol, optional clarifier-surfactant, optional zinc clarified, color, and fragrance components present.

| INGREDIENTS | PARTS BY WEIGHT |
|---|---|
| D.I. water | 37.00 |
| Sodium Bicarbonate Grade 3 (Church & Dwight) | 4.50 |
| Polymin-P (polyethylenimine by BASF) 50% active solids | 6.00 |
| Irgasan DP200 (triclosan by Ciba-Geigy) | 0.28 |
| Propylene Glycol | 40.55 |
| Clarit PDP 200 (Pentadoxynol-200 by RTD Chemicals Corp) | 2.50 |
| OP-100V (sodium stearate by RTD Chemicals Corp) | 2.50 |
| GE 1288 (dimethicone copolyol) | 4.50 |
| FD&C Green #5 (0.4% solution) | 0.25 |
| Fragrance | 1.50 |
| Zinc Omadine (48% solution) | 0.42 |

The ingredients are blended in the manner set forth above to yield a clear, transparent cosmetic deodorant stick product of the invention.

EXAMPLE IV

This Example illustrates a cosmetic stick product within the present invention, with an antibacterial, optional silicone polyol, optional clarifier-surfactant, color, and fragrance components present.

| INGREDIENTS | PARTS BY WEIGHT |
| --- | --- |
| D.I. water | 37.00 |
| Potassium Bicarbonate (Church & Dwight) | 4.50 |
| Polymin-P (polyethylenimine by BASF) 50% active solids | 6.00 |
| Irgasan DP 200 (triclosan) | 0.28 |
| Glycerin | 40.97 |
| Clarit PDP 200 (Pentadoxynol-200 by RTD Chemicals Corp) | 2.50 |
| Potassium palmitate | 2.50 |
| Silicone Copolymer F-754 (Wacker) | 4.50 |
| FD&C Green #5 (0.4% solution) | 0.25 |
| Fragrance | 1.50 |

The ingredients are blended in the manner set forth above to yield a clear, transparent cosmetic deodorant stick product of the invention.

EXAMPLE V

This Example illustrates a cosmetic stick product within the present invention, with an antibacterial, optional silicone polyol, color, and fragrance components present.

| INGREDIENTS | PARTS BY WEIGHT |
| --- | --- |
| D.I. water | 37.00 |
| Sodium Bicarbonate (Church & Dwight) | 4.50 |
| Polymin-P (polyethylenimine by BASF) 50% active solids | 6.00 |
| Irgasan (triclosan by Ciba-Geigy) | 0.28 |
| Propylene Glycol | 40.97 |
| Steareth-100 (PEG-100 stearyl ether - available as Brij 700 from ICI Americas) | 2.50 |
| Sodium palmitate | 2.50 |
| GE 1288 (dimethicone copolyol) | 4.50 |
| FD&C Green #5 (0.4% solution) | 0.25 |
| Fragrance | 1.50 |

The ingredients are blended in the manner set forth above to yield a clear, transparent cosmetic deodorant stick product of the invention.

EXAMPLE VI

This Example illustrates a cosmetic stick product of the art, with an antibacterial, optional silicone polyol, color, and fragrance components present. It differs from invention Example III only in that the zinc omadine is omitted (being replaced by additional propylene glycol), the polyamine component is missing, and the sodium stearate is increased to maintain hardness. On a parts by weight, it is identical with invention Example III in all other respects.

| INGREDIENTS | PARTS BY WEIGHT |
| --- | --- |
| D.I. water | 37.00 |
| Sodium Bicarbonate Grade 3 (Church & Dwight) | 4.50 |
| Irgasan DP200 (triclosan by Ciba-Geigy) | 0.28 |
| Propylene Glycol | 40.97 |
| Clarit PDP 200 (Pentadoxynol-200 by RTD Chemicals Corp) | 2.50 |
| OP-100V (sodium stearate by RTD Chemicals Corp) | 4.00 |
| GE 1288 (dimethicone copolyol) | 4.50 |
| FD&C Green #5 (0.4% solution) | 0.25 |
| Fragrance | 1.50 |

The ingredients are blended in the manner set forth above, as in Example IV. The product is not transparent, but only faintly translucent.

EXAMPLE VII

This Example illustrates a cosmetic stick product of the art similar to art Example VI. Whereas in art Example VI, the polyamine component of the invention product was merely omitted, resulting in a non-transparent product, in this Example, the polyamine component is replaced by additional water. In all other respects, this art Example is identical to art Example VI.

| INGREDIENTS | PARTS BY WEIGHT |
| --- | --- |
| D.I. water | 43.00 |
| Sodium Bicarbonate Grade 3 (Church & Dwight) | 4.50 |
| Irgasan DP200 (triclosan by Ciba-Geigy) | 0.28 |
| Propylene Glycol | 40.97 |
| Clarit PDP 200 (Pentadoxynol-200 by RTD Chemicals Corp) | 2.50 |
| OP-100V (sodium stearate by RTD Chemicals Corp) | 4.00 |
| GE 1288 (dimethicone copolyol) | 4.50 |
| FD&C Green #5 (0.4% solution) | 0.25 |
| Fragrance | 1.50 |

The ingredients are blended in the manner set forth above to yield a stick product which suffers from being translucent to opaque, being too soft, being very wet, and stability problems as the bicarbonate/carbonate component settles out over time and tends to foul manufacturing equipment.

EXAMPLE VIII

This Example illustrates a high bicarbonate cosmetic stick product within the present invention, with an antibacterial, optional silicone polyol, color, and fragrance components present.

| INGREDIENTS | PARTS BY WEIGHT |
| --- | --- |
| D.I. water | 36.00 |
| Sodium Bicarbonate Grade 3 (Church & Dwight) | 5.50 |
| Polymin-P (polyethylenimine by BASF) 50% active solids | 6.00 |
| Irgasan DP200 (triclosan by Ciba-Geigy) | 0.28 |
| Propylene Glycol | 40.97 |
| Clarit PDP 200 (Pentadoxynol-200 by RTD Chemicals Corp) | 2.50 |
| OP-100V (sodium stearate by RTD Chemicals Corp) | 2.50 |
| GE 1288 (dimethicone copolyol) | 4.50 |
| FD&C Green #5 (0.4% solution) | 0.25 |
| Fragrance | 1.50 |

The ingredients are blended in the manner set forth above to yield a clear, transparent cosmetic deodorant stick product of the invention.

EXAMPLE IX

This Example illustrates a high bicarbonate cosmetic stick product within the present invention, with an antibacterial, optional silicone polyol, color, and fragrance components present.

| INGREDIENTS | PARTS BY WEIGHT |
| --- | --- |
| D.I. water | 37.00 |
| Sodium Bicarbonate Grade 3 (Church & Dwight) | 4.50 |
| Polymin-P (polyethylenimine by BASF) 50% active solids | 4.50 |
| Polymin-PL (polyethylenimine by BASF) 25% active solids | 3.13 |
| Dipropylene Glycol | 1.00 |
| Irgasan DP200 (triclosan by Ciba-Geigy) | 0.28 |
| Propylene Glycol | 37.67 |
| Clarit PDP 200 (Pentadoxynol-200 by RTD Chemicals Corp) | 2.50 |
| OP-100V (sodium stearate by RTD Chemicals Corp) | 3.50 |
| GE 1288 (dimethicone copolyol) | 4.50 |
| Fragrance | 1.00 |
| Zinc Omadine (48% solution) | 0.42 |

The ingredients are blended as follows:

First the water is heated to 60° C. in a first vessel. The zinc omadine is added to the first vessel and mixed well. Then the Polymin P and Polymin PL are added to the first vessel while still maintaining the temperature at 60° C. Meanwhile, in a second vessel, the propylene glycol is heated to 80° C. While maintaining the second vessel at 75°–80° C., the triclosan is added to the second vessel. Next, the pentadoxynol is added to the second vessel while the vessel is maintained at 80° C., and the pentadoxynol is allowed to completely dissolve. The dimethicone copolyol is then added to the second vessel.

To the first vessel, now add the sodium bicarbonate and mix well. Slowly (with a spatula) add the sodium stearate to the second vessel. Slowly add the contents of the first vessel to that of the second vessel and allow the mixture to cool to 65°–70° C. If color is desired (not present in the above formula) it should be added at this point. Finally, the fragrance is added to the second vessel and the mixture is poured into canisters to give a product of the present invention. Any bubbles can be removed using a heat gun.

We claim:

1. A transparent, bicarbonate salt containing deodorant stick product comprising:

(1) an alkali metal bicarbonate and/or an alkali metal carbonate or species which are convertible in situ into said bicarbonate or carbonate in amounts such that the following relationship is satisfied:

$$7.0 < (2(\text{alkali metal bicarbonate wt \%}) + (\text{alkali metal carbonate wt \%})) \leq 11.0;$$

(2) about 35% to about 55% by weight of a polyhydric alcohol;

(3) about 1.25% to about 6.5% by weight of a polyamine clarifier; and (4) about 1.25% to about 5% by weight of a $C_{14-22}$ fatty acid salt; and (5) water in an amount less than about 42% by weight; and optionally (6) one or more ingredients selected from the group consisting of an underarm deodorant acceptable antibacterial or bacteriostatic agent, a silicone copolyol; zinc pyridinethiol oxide, fragrance, color and about 2% to about 10% by weight of a clarifier surfactant, all weight percents as used herein being based on the finished stick product weight wherein said polyamine clarifier is selected from the group consisting of polyalkylenimines having a weight average molecular weight between about 800 and about 1,000,000 and a partial structure of formula I:

where R1 is hydrogen or a $C_{1-3}$ alkyl group and n is an integer of from 2 to 6.

2. The product of claim 1 wherein said alkali metal bicarbonate salt is sodium bicarbonate.

3. The product of claim 1 wherein said alkali metal bicarbonate and/or an alkali metal carbonate or species which are convertible in situ into said bicarbonate or carbonate is sodium bicarbonate.

4. The product of claim 1 wherein said alkali metal bicarbonate is present in an amount of about 4.5% by weight.

5. The product of claim 3 wherein said alkali metal bicarbonate is present in an amount of about 4.5% by weight.

6. The product of claim 1 wherein said polyhydric alcohol is selected from the group consisting of organic compounds which contain about 2 to about 6 carbon atoms and about 2 to about 6 hydroxy groups.

7. The product of claim 1 wherein said polyhydric alcohol is selected from the group consisting of ethylene glycol, propylene glycol, trimethylene glycol, butylene glycol, diethylene glycol, dipropylene glycol, glycerin, sorbitol and mixtures thereof.

8. The product of claim 1 wherein said polyhydric alcohol is propylene glycol or dipropylene glycol or a mixture thereof.

9. The product of claim 1 wherein said polyhydric alcohol is a propylene glycol/dipropylene glycol mixture.

10. The product of claim 1 wherein said polyhydric alcohol is present in an amount of about 40% to about 45% by weight.

11. The product of claim 1 wherein said clarifier-surfactant is present in an amount of about 2.0% to about 3.0% by weight.

12. The product of claim 1 wherein said polyamine is a homopolymer of units of structural formula I, R1 is hydrogen and n is 2, and the number of repeating units of structural formula I is, on average about 1450 to about 1550.

13. The product of claim 1 wherein said polyamine clarifier is present in an amount of from about 2.5% to about 3.5% by weight.

14. The product of claim 1 wherein said fatty acid salt is selected from the group consisting of alkali metal, alkaline earth metal, aluminum, and amine salts of $C_{14-22}$ fatty acids.

15. The product of claim 1 wherein said $C_{14-22}$ fatty acid salt is selected from the group consisting of salts of myristic, palmitic, stearic, behenic, oleic, linoleic, and linolenic acids and mixtures thereof.

16. The product of claim 1 wherein said $C_{14-22}$ fatty acid salt is selected from the group consisting of sodium stearate, potassium stearate, aluminum monostearate, sodium oleate, sodium palmitate, sodium behenate, diethylamine stearate, triethylamine stearate, and triethylemine oleate, and mixtures thereof.

17. The product of claim 1 wherein said $C_{14-22}$ fatty acid salt is sodium stearate.

18. The product of claim 1 wherein said $C_{14-22}$ fatty acid salt is present in an amount of from about 2.2% to about 3.5% by weight.

19. The product of claim 1 wherein said clarifier-surfactant is selected from the group consisting of pentadoxynol-200, tetra(hydroxypropyl)diamine, 2-amino-2-methylpropanol, 2-amino-2-hydroxymethyl-1,3-propanediol, poly($C_{2-4}$alkylene) glycol ethers of $C_{12-22}$ fatty alcohols in which the polyalkylene glycol portion contains from about 10 to about 100 alkyleneoxide repeating units.

20. The product of claim 1 wherein said clarifier-surfactant is selected from the group consisting of laureth-10, laureth-20, laureth-30. laureth-40, PEG-10 Myristyl Ether, steareth-10, steareth-20, steareth-40, steareth-100, PEG-50 Stearyl Ether, steareth-100 and beheneth-20,and mixtures thereof.

21. The product of claim 1 wherein said clarifier-surfactant is polyoxyethylene 3-pentadecyl phenyl ether.

22. The product of claim 1 which is

| INGREDIENTS | APPROXIMATE PARTS BY WEIGHT |
| --- | --- |
| water | 37.00 |
| sodium bicarbonate | 4.50 |
| polyethylenimine (50% active solids) 1500 ethylenimine units/molecule average | 6.00 |
| triclosan | 0.28 |
| propylene glycol | 40.55–41.97 |
| polyoxyethylene [200] 3-pentadecyl phenyl ether | 2.50 |
| sodium stearate | 2.50 |
| dimethicone copolyol | 4.00–4.50 |
| Colorant | 0.25–0.5 |
| Fragrance | 1.0–1.50 |
| zinc 2-pyridinethiol-1-oxide (48% solution) | 0.0–0.42. |

23. The product of claim 1 which is

| INGREDIENTS | APPROXIMATE PARTS BY WEIGHT |
| --- | --- |
| water | 37.00 |
| Sodium bicarbonate Grade 3 (Church & Dwight) | 4.50 |
| Polymin-P (polyethylenimine by BASF) 50% active solids | 4.50 |
| Polymin-PL (polyethylenimine by BASF) 25% active solids | 3.13 |
| Dipropylene Glycol | 1.00 |
| Irgasan DP200 (triclosan by Ciba-Geigy) | 0.28 |
| Propylene Glycol | 37.67 |
| Clarit PDP 200 (Polyoxyethylene [200] 3-pentadecyl phenyl ether by RTD Chemicals Corp.) | 2.50 |
| OP-100V (sodium stearate by RTD Chemicals Corp.) | 3.50 |
| GE 1288 (dimethicone copolyol) | 4.50 |
| Fragrance | 1.00 |
| Zinc 2-pyridinethiol-1-oxide (48% solution) | 0.42. |

24. A method of making a transparent, bicarbonate containing deodorant cosmetic stick product comprising incorporating into said stick a polyamine clarifier selected from the group consisting of polyalkylenimines having a weight average molecular weight between about 800 and about 1,000,000 and a partial structure of formula I:

where R1 is hydrogen or a $C_{1-3}$alkyl group and n is an integer of from 2 to 6.

* * * * *